United States Patent [19]

Bittner et al.

[11] Patent Number: 5,673,842
[45] Date of Patent: Oct. 7, 1997

[54] SURGICAL STAPLER WITH LOCKING MECHANISM

[75] Inventors: John R. Bittner, Loveland; Peter Lau, Cincinnati, both of Ohio

[73] Assignee: Ethicon Endo-Surgery, Cincinnati, Ohio

[21] Appl. No.: 611,161

[22] Filed: Mar. 5, 1996

[51] Int. Cl.$^6$ ............................................. A61B 17/068
[52] U.S. Cl. ........................... 227/175.4; 227/175.2; 227/180.1
[58] Field of Search ................. 227/175.2, 175.3, 227/175.4, 176.1, 178.1, 180.1, 8, 19

[56] References Cited

U.S. PATENT DOCUMENTS

| | | | |
|---|---|---|---|
| 4,892,244 | 1/1990 | Fox et al. | 227/8 |
| 4,955,959 | 9/1990 | Tompkins et al. | 227/178.1 |
| 5,129,570 | 7/1992 | Schulze et la. | 227/19 |
| 5,485,947 | 1/1996 | Olson et al. | 227/176.1 |
| 5,584,425 | 12/1996 | Savage et al. | 227/175.2 |

*Primary Examiner*—Joseph J. Hail, III
*Assistant Examiner*—Jay A. Stelacone
*Attorney, Agent, or Firm*—Dressler, Rockey, Milnamow & Katz, Ltd.

[57] ABSTRACT

A surgical stapler for effecting simultaneous cutting and stapling of tissue includes a frame and a staple cartridge positionable in the frame. The stapler includes a knife blade mounted for movement distally of the staple cartridge, with the cartridge including a rotatable member which cooperates with the knife blade for preventing use of the stapler unless it is fitted with a fresh, unused staple cartridge. The rotatable member on the staple cartridge is configured to facilitate convenient and efficient use of the stapler by reducing the force required for operation of the device.

8 Claims, 6 Drawing Sheets

SURGICAL STAPLER WITH LOCKING MECHANISM

TECHNICAL FIELD

The present invention relates generally to a surgical stapler that prevents reuse of a previously used staple cartridge, and more particularly to a surgical stapler having a locking mechanism that prevents such reuse, while minimizing the force required for actuating the stapler.

BACKGROUND OF THE INVENTION

U.S. Pat. No. 5,129,570, hereby incorporated by reference, discloses a surgical stapler configured for applying rows of staples in lieu of suturing tissue. This type of surgical device greatly facilitates surgical procedures, and desirably reduces the time otherwise required for suturing tissue.

The surgical stapler disclosed in the above-referenced patent is configured to employ a removable staple cartridge, which typically includes a plurality of rows of staples. Attendant to each use of the surgical stapler, a fresh, unused staple cartridge is inserted into a frame of the stapler, with the device then positioned for use for suturing tissue. The stapler includes one or more firing wedges which can be advanced through the staple cartridge, and which cooperate in a cam-like manner with drivers within the cartridge to fire the staples, driving them through tissue and against an associated anvil of the stapler for closing the staples. For reuse, the firing wedges are retracted, the used staple cartridge removed, and an unused staple cartridge inserted into the device.

While some staplers are configured to perform the sole function of stapling, one particularly useful configuration of a surgical stapler effects simultaneous cutting and stapling (i.e., suturing) of tissue. Such devices, sometimes referred to as linear cutters, include a knife blade which is advanced together with the firing wedges of the surgical stapler during use. In this manner, cutting of tissue is effected simultaneously with stapling, greatly facilitating efficiency in surgical procedures.

In order to preclude inadvertent use of a stapler with a used staple cartridge, thereby avoiding inadvertent cutting of tissue without simultaneous application of staples, surgical staplers are ordinarily provided with locking mechanisms which prevent actuation of the device unless fitted with a fresh, unused staple cartridge. U.S. Pat. No. Re. 34,519, to Fox et al., hereby incorporated by reference, discloses various embodiments of such locking mechanisms, with the above-referenced U.S. Pat. No. 5,129,570 disclosing further embodiments of such locking mechanisms.

In the locking mechanisms disclosed in U.S. Pat. No. 5,129,570, the knife blade of the illustrated surgical stapler is configured to cooperate with a member provided on an unused staple cartridge for permitting advancement of the knife blade, and actuation of the stapler, when fitted with the unused cartridge. In particular, the knife blade is mounted for limited vertical movement in opposition to a biasing spring, which spring ordinarily urges the knife blade into a locked position in association with a roof member of the stapler. Insertion of an unused staple cartridge into the device acts to displace the knife blade, in opposition to the biasing spring, into alignment with a slot defined by the roof member. This permits advancement of the knife blade and the associated firing wedges of the stapler, thus permitting simultaneous cutting and stapling of tissue. During advancement of the knife blade, the cooperating member on the staple cartridge is displaced. As a consequence, upon retraction of the knife blade and firing wedges, the knife blade is urged by the biasing spring into engagement with the roof member and out of alignment with the slot therein, thus preventing reuse of the device until fitted with an unused staple cartridge.

Experience has shown that while the above-described locking mechanism is highly effective, displacement of the staple-mounted member, which acts against the knife blade, requires application of a degree of force by the surgeon which detracts from convenient use of the stapler.

In particular, current commercial embodiments of surgical staplers in accordance with the above-referenced patent include a rotatable member mounted on the staple cartridge for cooperation with the associated knife blade. This rotatable member (sometimes referred to as a swing tab) is configured to interferingly engage the body of the staple cartridge as the member is rotated by the knife blade, thus providing a snap-over like action to maintain the rotatable member in an out-of-the-way disposition. This prevents the knife blade from engaging the rotatable member and returning to its original position as the blade is retracted. However, the surgeon operating the stapler perceives this interfering snap-over of the rotatable member as an undesirable increase in the so-called "force to fire" the stapler.

A surgical stapler, and staple cartridge, embodying the principles of the present invention are particularly configured to reduce this "force to fire", thus further facilitating convenient and efficient use of such surgical staplers.

SUMMARY OF THE INVENTION

A surgical stapler embodying the principles of the present invention includes a staple cartridge having a rotatable member which is initially positioned to coact with a knife blade of the surgical stapler to position the knife blade for distal movement in the device, thus permitting actuation for simultaneous cutting and stapling of tissue. Notably, the rotatable member is specifically configured to move to an out-of-the-way disposition during actuation of the device without application of undue force to the rotatable member. Convenient and efficient use is facilitated by the resultant reduction in "force to fire" of the stapler.

In accordance with the illustrated embodiment, the present surgical stapler comprises a frame, and a staple cartridge positionable in the frame. The staple cartridge comprises a cartridge body containing at least one row of staples, with the cartridge defining an elongated knife slot. At least one firing wedge is carried by the frame of the surgical stapler for movement longitudinally of the stapler. Such longitudinal movement, distally of the stapler, effects sequential driving of the staples from the staple cartridge through tissue and against an associated anvil of the stapler.

A knife blade is carried by the frame of the stapler for movement through the elongated knife slot defined by the staple cartridge. The knife blade is also vertically movable between a first, locked position wherein the knife blade is substantially prevented from moving through the knife slot, and a second, unlocked position wherein the knife blade is movable through the slot in the staple cartridge.

The staple cartridge includes a rotatable member which is movable from a first position to a second position. In its first position, the rotatable member is engageable with the knife blade as the staple cartridge is positioned in the frame of the stapler. This engagement acts to move the knife blade from its first, locked position to its second, unlocked position.

During actuation of the stapler, the rotatable member on the cartridge is moved to the second position thereof by the knife blade as the knife blade is advanced distally of the cartridge through the knife slot. Simultaneous cutting and stapling of tissue is effected during distal advancement of the knife blade.

The rotatable member on the staple cartridge includes a resiliently flexible portion which is yieldably engageable with the body of the staple cartridge as the rotatable member is moved from its first position to its second position. After such movement, the flexible portion on the rotatable member is engageable with the cartridge body to maintain the rotatable member in the second position thereof. Upon retraction of the knife blade, the blade returns to its first, locked position wherein it is substantially prevented from movement through the knife slot (i.e., its position prior to insertion of an unused staple cartridge). This takes place since the rotatable member on the staple cartridge has been moved to its second position, and thus is no longer engageable with the knife blade. Reuse of the stapler is effected by removal of the spent cartridge, and insertion of a fresh, unused staple-filled cartridge.

In accordance with the illustrated embodiment, a first end portion of the rotatable member is pivotally mounted on the cartridge body of the staple cartridge. The resiliently flexible portion of the member comprises a cantilevered arm at this first end portion, which arm is engageable with the cartridge body as the rotatable member is moved from its first to its second position. Additionally, the rotatable member preferably comprises a cam projection engageable by the knife blade of the stapler as the knife blade is advanced distally through the knife slot. The cam projection facilitates movement of the rotatable member to the second position thereof. In the preferred embodiment, the cam projection is provided generally at a second end portion of the rotatable member, spaced from the first end portion thereof.

Other features and advantages of the present invention will become readily apparent from the following detailed description, the accompanying drawings, and the appended claims.

DETAILED DESCRIPTION

Figure 1:
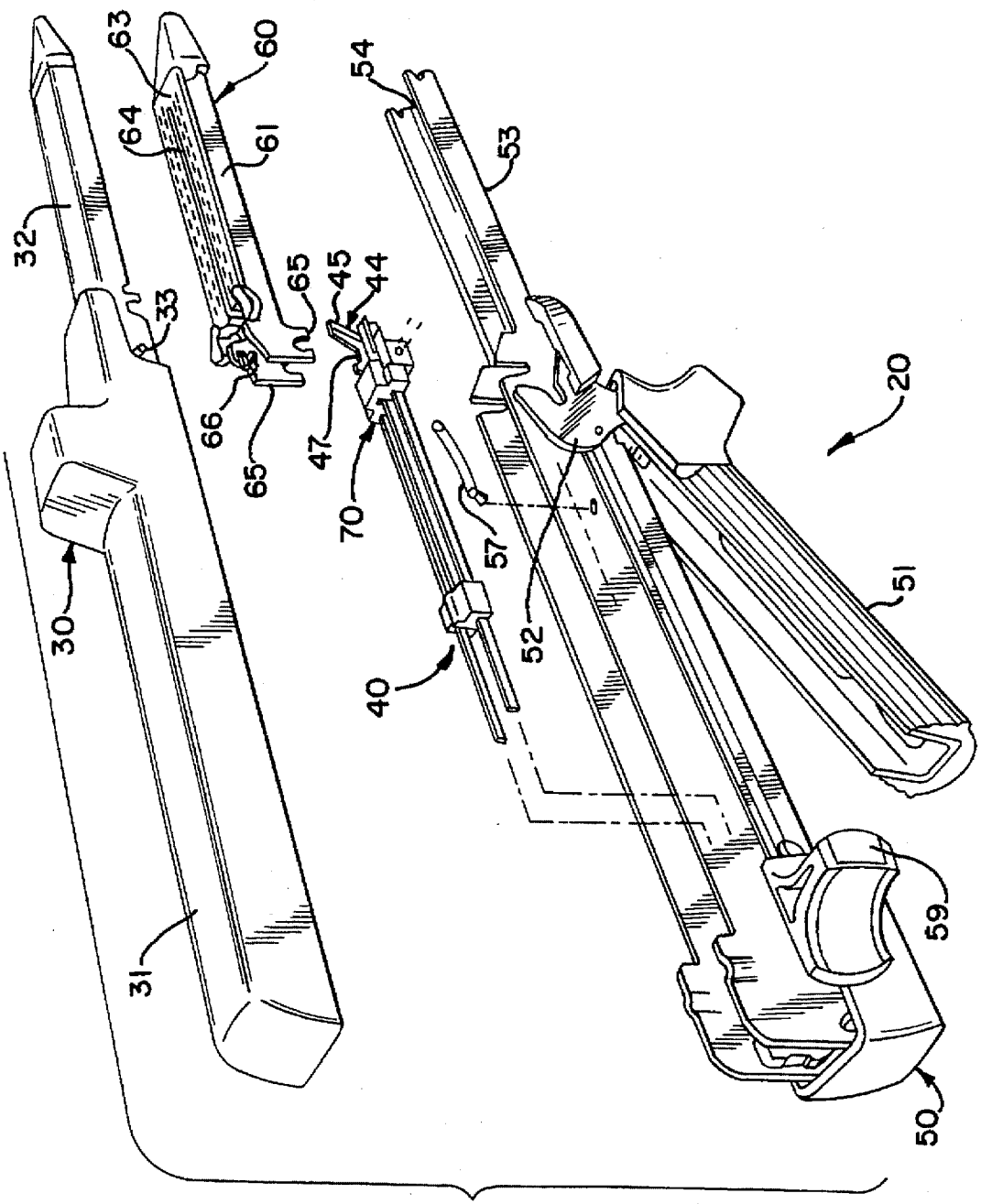
FIG. 1 is an exploded perspective view of a surgical stapler embodying the principles of the present invention.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

Figure 8:
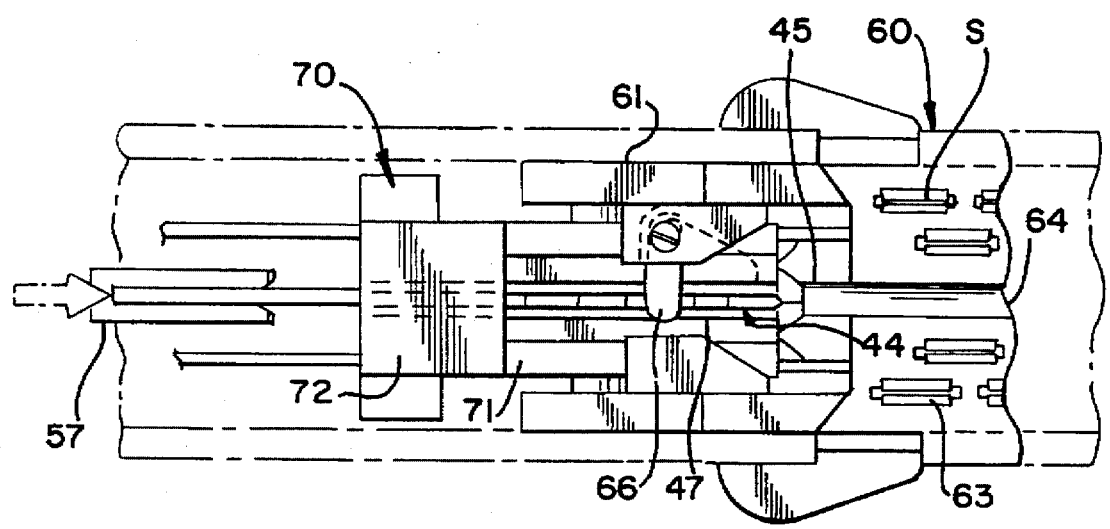
FIG. 8 is a fragmentary top plan view taken along line 8—8 of FIG. 6 showing the knife blade prior to actuation of the stapler.
Figure 9A:
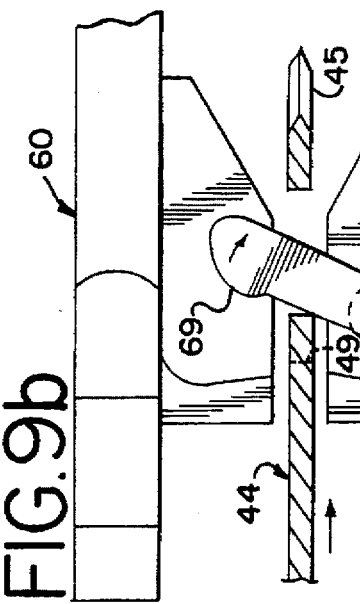
FIGS. 9a to 9d are fragmentary, bottom plan views illustrating the rotatable member of the locking mechanism as it is moved from a first to a second position thereof by the associated cutting knife blade of the surgical stapler.
Figure 9B:
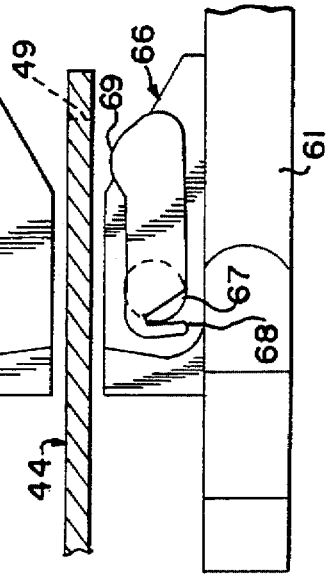
Figure 9C:
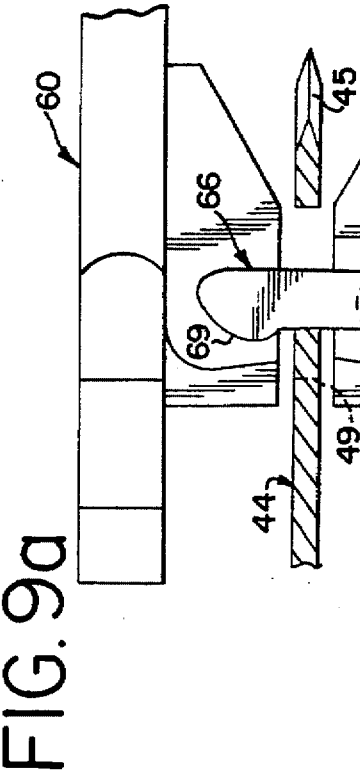
Figure 9D:
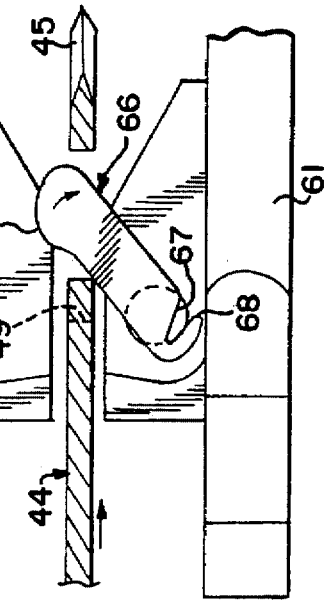

As illustrated in FIG. 1, a surgical stapler 20 embodying the principles of the present invention comprises an upper frame piece 30, a firing or pusher assembly 40, a lower frame piece 50, and a removable staple cartridge 60. Upper and lower frame pieces 30 and 50 collectively provide a frame of the stapler, with the firing assembly 40 carried by the frame for movement longitudinally of the staple cartridge for effecting sequential driving of staples S (FIG. 8) from the cartridge.

Figure 2:
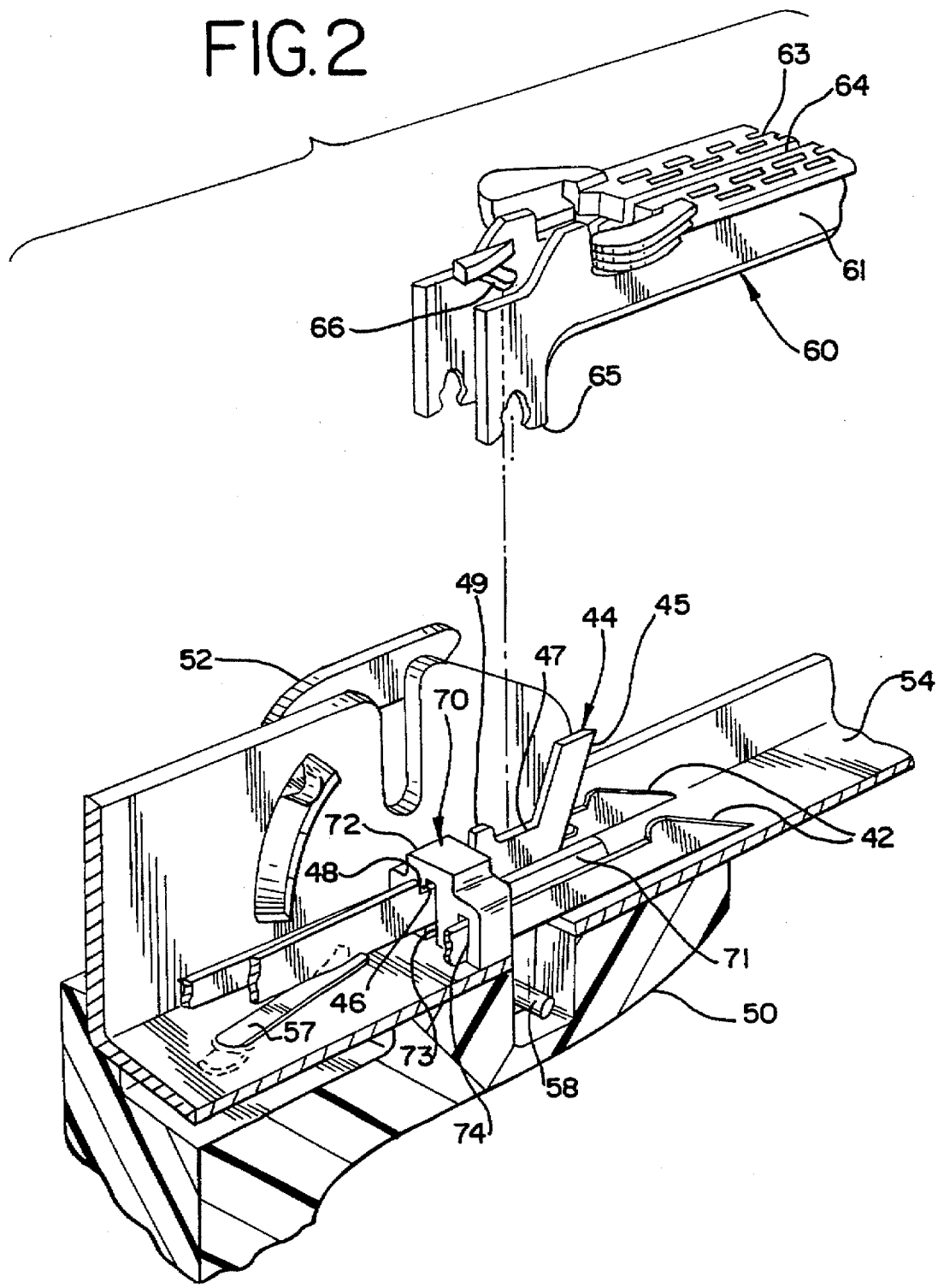
FIG. 2 is an exploded perspective view illustrating a locking mechanism, partially broken away, of the present surgical stapler.

The staple cartridge 60 fits within lower frame piece 50. Specifically, the front part of the staple cartridge 60 fits into a lower jaw 53 defining a channel 54, with the parallel side walls of the cartridge body 61 of the staple cartridge 60 fitted within the lower jaw channel 54. The back or proximal portion of the staple cartridge 60 has a rotatable member 66, embodying the principles of the present invention, which initially extends in a first position generally transversely of the staple cartridge. As will be further described, the rotatable member 66 is engageable with a knife blade 44 of the firing assembly 40. Attendant to disposition of the staple cartridge in the lower frame piece of the stapler, two legs 65 of the staple cartridge secure the cartridge to the lower frame piece 50. These legs 65 engage cylindrical pin 58 of lower frame piece 50, as illustrated in exploded perspective view in FIG. 2.

As illustrated in FIG. 1, the upper frame piece 30 has a rear upper handle portion 31 and a front upper jaw portion 32 which defines an anvil against which the staples in cartridge 60 are driven. The lower frame piece 50 includes a pivotable lower handle portion 51 positioned rearwardly of the lower jaw portion 53. In the illustrated embodiment, the longitudinally movable firing assembly 40, a biasing leaf spring 57, and the staple cartridge 60 are fitted in the lower frame piece 50. It is within the purview of the present invention to otherwise position these components in either one of the upper and lower frame pieces.

The lower handle portion 51 is pivotally movable between two positions. In a first open position of the lower handle portion 51, the handle portion extends at an angle with respect to lower jaw portion 53. In this position of the handle portion, a pair of C-shaped members 52 of the handle portion 51 are disengaged from a stationary locking pin 33 (FIG. 1) mounted on upper frame piece 30. In this position of the handle portion, the upper and lower frame pieces 30, 50 can be separated from each other, permitting insertion and removal of staple cartridge 60.

In the second, locking position of the lower handle portion 51, the C-shaped members 52 engage the locking pin 33, thus locking the upper and lower frame pieces 30 and 50 together. In this locking position, the movable handle portion 51 is positioned in generally parallel relationship to the lower jaw portion 53.

The firing or pusher assembly 40 comprises at least one pusher bar or firing wedge 42 (see FIG. 2), with the illustrated embodiment including two such firing wedges. A firing or actuation knob 59 (FIG. 1) is operatively joined to the firing assembly 40 for effecting longitudinal movement of the firing wedges 42 longitudinally through the staple cartridge 60 when an unused staple cartridge has been positioned in lower jaw portion 53, and the upper and lower frame pieces 30, 50 secured to each other by locking engagement of C-shaped members 52 with locking pin 33.

Figure 3:
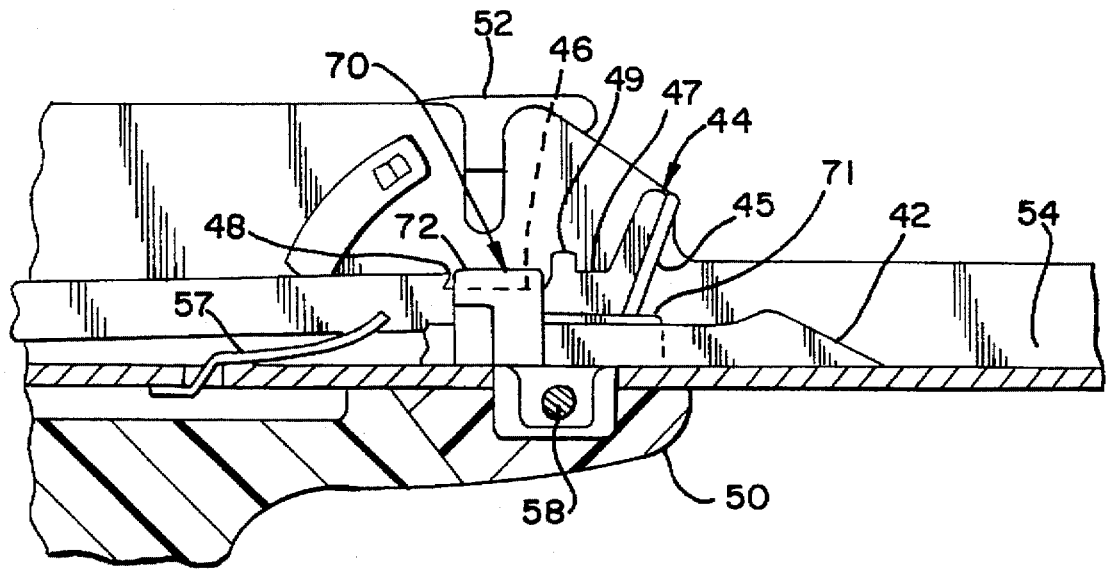
FIG. 3 is a side elevational view, in partial cross-section, illustrating the present surgical stapler prior to insertion of a staple cartridge therein, showing a cutting knife blade of the stapler in a locked, first position.
Figure 4:
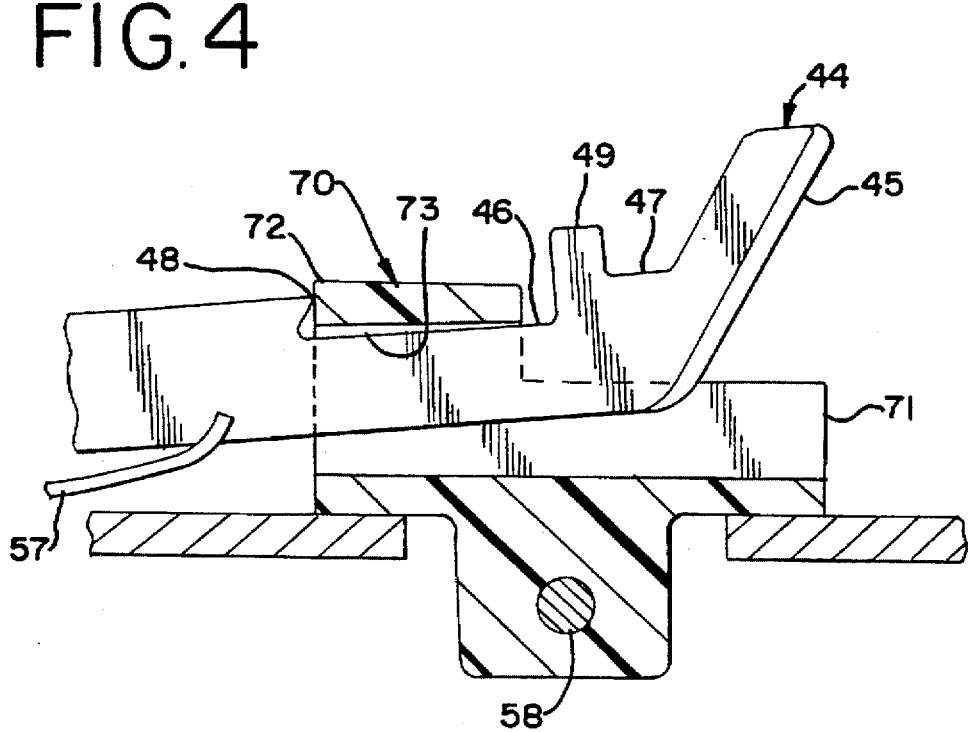
FIG. 4 is an enlarged detailed view in partial cross-section showing the locking mechanism locking the cutting knife blade in the first position thereof.

The locking mechanism of the present surgical stapler is intended to prevent use of the device unless the frame is fitted with an unused staple cartridge 60. The locking mechanism includes a roof member 70 (FIG. 2) having a distally extending narrow roof portion 71 (FIGS. 3, 4). The roof portion 71 is integral with a widened roof portion 72 defining three slots. Knife slot 73 extends through the widened roof portion 72 and the narrow roof portion 71. The roof portion 72 defines two additional slots 74 through which firing wedges 42 respectively extend. The narrow roof portion 71 is positioned generally between the firing wedges 42. As firing wedges 42 slide through slots 74, knife blade 44 is movable distally through slot 73. The knife blade 44 includes a cutting surface 45, with the disposition of the knife blade between the illustrated firing wedges 42 configuring the present stapler for cutting of tissue while one or more rows of staples are simultaneously placed on each side of the cut tissue.

Figure 5:
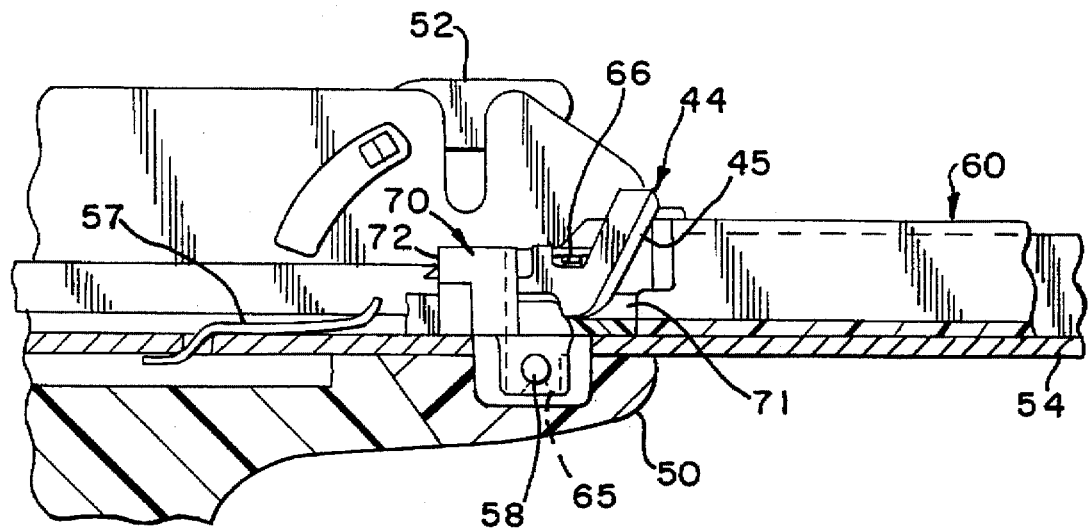
FIG. 5 is a view similar to that of FIG. 3 with a staple cartridge in place.

Not only is the knife blade 44 movable distally of the surgical stapler for effecting tissue cutting, the knife blade is also movable generally vertically between a first, locked position and a second, unlocked position thereof. In the first position of the knife blade assembly, illustrated in FIGS. 3 and 4, the knife blade assembly is out of alignment with knife slot 73 defined by roof member 70, thus preventing movement of the knife blade 44 through the roof member, and through an elongated knife slot 64 defined by the body of the staple cartridge 60. Biasing leaf spring 57 ordinarily urges the knife blade 44 upwardly into this first, locked position. The knife blade 44 is movable vertically in opposition to the leaf spring 57 to a second, unlocked position of the knife blade. In this second position (FIGS. 5 and 6), the knife blade is positioned in alignment with knife slot 73, and is thus positioned for advancement distally through slot 73 in the roof member, and through knife slot 64 defined by staple cartridge 60.

Figure 6:
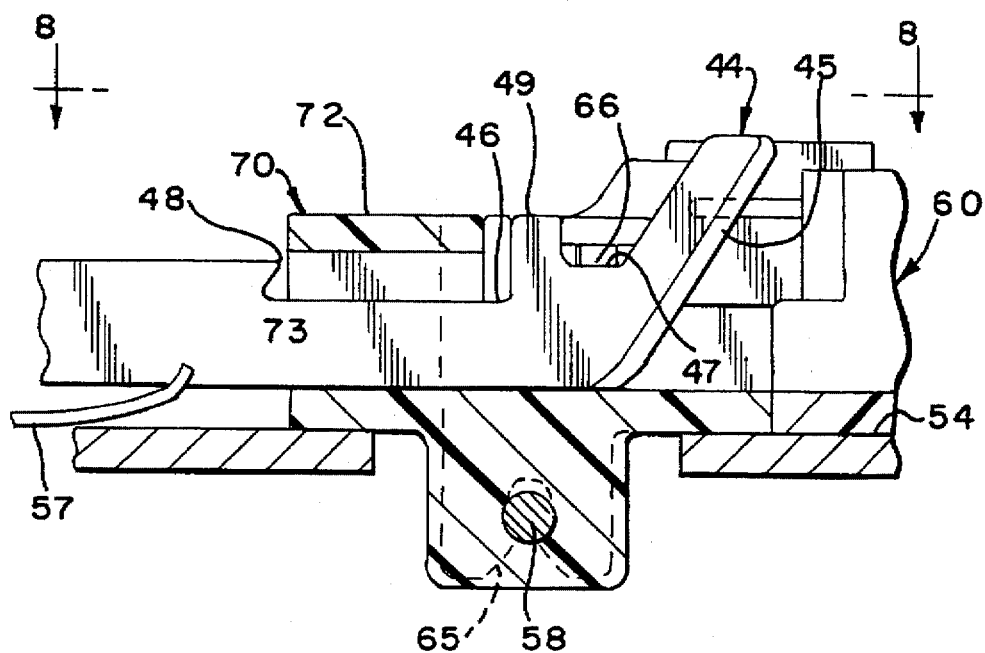
FIG. 6 is an enlarged detailed view in partial cross-section showing the cutting knife blade in a second, unlocked position thereof.
Figure 7:
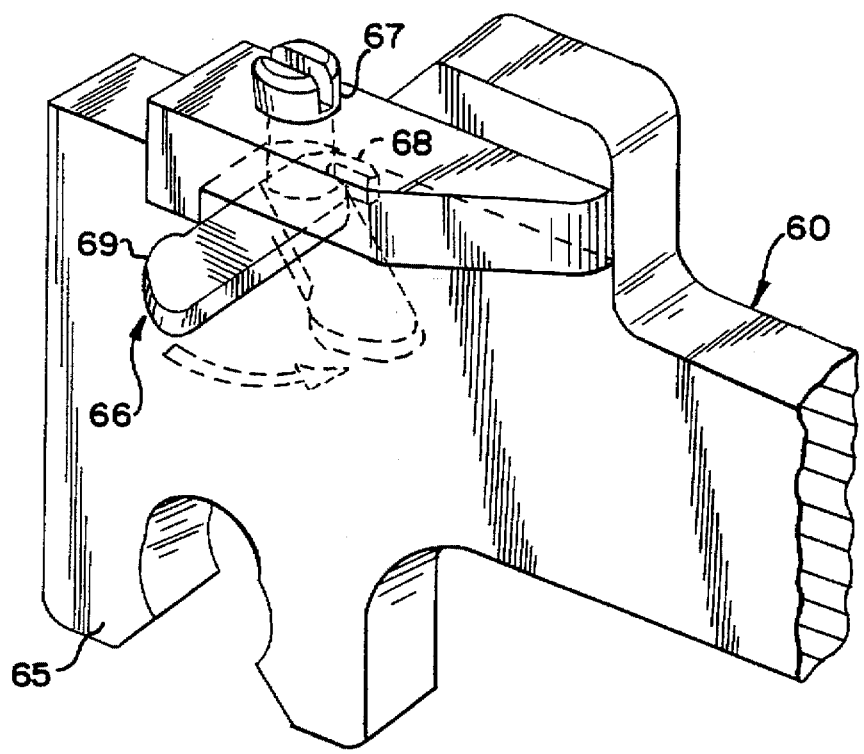
FIG. 7 is a fragmentary perspective view of a rotatable member of the locking mechanism of the present invention.

The specific cooperation of the knife blade 44 and the roof member 70 is best illustrated in FIGS. 4 and 6. As shown in FIG. 4, illustrating the first, locked position of the knife blade 44, leaf spring 57 pushes the knife blade up against roof member 70. Widened roof portion 72 engages a locking area 46 of the knife blade, with engagement of a locking portion 48 of the knife blade with the roof member 70 preventing distal movement of the knife blade through the roof member and through the elongated knife slot 64 of the staple cartridge. In this position of the knife blade, the firing wedges 44 of the firing assembly 40 are also substantially prevented from forward movement, since the knife blade and firing wedges (i.e., firing assembly 40) are generally movable in unison.

Movement of the knife blade 44 from its first position to its second, unlocked position, for advancement, is effected by disposition of an unused staple cartridge 60 in the channel 54 of lower jaw portion 53. The rotatable member 66, pivotably mounted by integral pin 67 on the body 61 of the staple cartridge 60, is engageable with the knife blade 44 at surface 47. As the staple cartridge is lowered into the lower jaw portion, the rotatable member 66 acts on the knife blade 44 in opposition to biasing leaf spring 57, thereby unlocking the knife blade by movement downwardly to its second position. As will be observed in FIG. 6, wherein the knife blade 44 is illustrated in its second, unlocked position, locking portion 48 is moved from a position for engagement with roof member 70, with the knife blade 44 thus aligned with slot 73 to accommodate distal movement of the knife blade. In this position of the knife blade, the knife blade and the firing wedges 42 are movable together distally of the stapler, thereby effecting sequential driving of staples S (via staple drivers 63; see FIG. 8) from the cartridge 60 as the cutting surface 45 of the knife blade effects tissue cutting by movement through the elongated knife slot 64 defined by the staple cartridge 60.

With particular reference to FIG. 7, and FIGS. 9a to 9d, features of the rotatable member 66 and its cooperation with the knife blade 44, are illustrated. As noted, the rotatable member 66 initially engages the knife blade 44, thereby urging the knife blade from its first to its second position, when the firing assembly 40 (including knife blade 44 and firing wedges 42) is in its retracted position. As the knife blade 44 is advanced distally of the stapler, upstanding portion 49 of the knife blade engages the rotatable member 66. This engagement acts to rotate the member 66 from its first position (FIG. 9a) to its second position (FIG. 9d), wherein the rotatable member is maintained in an out-of-the-way disposition with respect to the knife blade.

As the member 66 rotates, the member engages the body 61 of the staple cartridge 60 as the member moves to its second position. Such engagement is desirable since it acts to maintain the rotatable member in its second position after the knife blade has been advanced distally through the staple cartridge. However, such rotatable movement of member 66 is, of course, effected by the user of the stapler, and thus the force required for movement of the member from its first to its second position must be exerted by the user through the firing knob 59 and the firing assembly 40.

In order to reduce the "force to fire" exerted by the user of the stapler, the rotatable member 66 has been specifically configured to accommodate movement from its first to its second position. Specifically, the rotatable member 66 includes a resiliently flexible portion 68 which is yieldably engageable with the body of the staple cartridge as the rotatable member is moved from its first position to its second position. The flexible portion 68 is preferably provided in the form of a cantilevered arm positioned at a first end portion of the rotatable member. As will be observed, the rotatable member 66 is pivotally mounted on the cartridge body 61 at this first end portion. Engagement of the flexible portion 68 with the cartridge body is particularly illustrated in FIGS. 9b and 9c.

In order to assure movement of the rotatable member 66 to its second position, the rotatable member preferably comprises a cam projection 69 engageable by portion 49 of the knife blade 44 as the knife blade is advanced distally through the knife slot of the staple cartridge. Once the rotatable member has been moved to its second position, the free end portion of the cantilevered flexible portion 68 is positioned in generally confronting relationship with the cartridge body (see FIG. 9d). In this orientation of the flexible portion 68, the flexible member is positioned for engagement with the cartridge body so that movement of the rotatable member from its second position is substantially prevented. As will be appreciated, the cantilevered flexible portion extends from its base in a direction away from the direction of rotation of the member 66 about its pivot pin 67.

In the preferred embodiment, the free end of the pivot pin 67 is bifurcated to render the pin resiliently compressible. The pin 67 can thus be compressed for insertion through the cartridge body 61, with the bifurcated portion of the pin 67 thereafter expanding outwardly to securely retain the rotatable member 66 on the cartridge body.

Upon retraction of firing assembly 40, including knife blade 44, the knife blade 44 returns to its locked position with respect to roof member 70. Rotatable member 66 remains in its second position, and thus does not engage portion 47 of the knife blade 44, with leaf spring 57 thus urging the knife blade upwardly with respect to the roof member so that locking portion 48 is positioned for engagement with the roof member. The handle 51 of the surgical stapler can be pivoted to unlock the upper and lower frame pieces of the stapler, thereby permitting separation of the frame pieces and removal of the used staple cartridge 60. Insertion of a fresh, unused staple cartridge 60 into the lower jaw portion 53 of the lower frame piece effects unlocking movement of the knife blade 44, by virtue of the rotatable member 66 of the unused cartridge being in the first position of the member 66. Engagement of the member 66 with the knife blade 44 at 47 moves the knife blade from its first, locked position to its second, unlocked position, with subsequent joining of the upper and lower frame pieces 30, 50, and locking of the frame pieces by movement of handle 51, thereafter preparing the stapler for reuse.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover all such modifications as fall within the scope of the appended claims.

What is claimed:

1. A surgical stapler comprising:
   a frame;
   a staple cartridge positionable in said frame and comprising a cartridge body containing at least one row of staples, said cartridge defining an elongated knife slot;
   at least one firing wedge carried by said frame for movement longitudinally of said staple cartridge for effecting sequential driving of said staples from said cartridge; and
   a knife blade carried by said frame for movement through said elongated knife slot; said knife being movable between a first position wherein said knife is substantially prevented from moving through said knife slot, and a second position wherein said knife is movable through said slot,
   said staple cartridge including a rotatable member movable from a first position to a second position, wherein in said first position, said rotatable member is engageable with said knife blade as said cartridge is positioned on said frame to move said knife blade from said first position to said second position, said rotatable member being moved to said second position thereof by said knife blade as said knife blade is advanced distally of said cartridge through said knife slot,
   said rotatable member including a resiliently flexible portion yieldably engageable with said cartridge body as said rotatable member is moved from said first position to said second position thereof, said flexible portion thereafter being engageable with said cartridge body to maintain said rotatable member in said second position thereof.

2. A surgical stapler in accordance with claim 1, wherein a first end portion of said rotatable member is pivotally mounted on said cartridge body, and said flexible portion of said rotatable member comprises a cantilevered arm at said first end portion.

3. A surgical stapler in accordance with claim 1, wherein said rotatable member comprises a cam projection engageable by said knife blade as said knife blade is advanced distally through said knife slot to facilitate movement of said rotatable member to said second position thereof.

4. A surgical stapler in accordance with claim 3, wherein said rotatable member includes a first end portion pivotally mounted on said cartridge body, said cam projection being provided generally at a second end portion of said rotatable member spaced from said first end portion.

5. A staple cartridge of a surgical stapler having a frame, and a knife blade movable between a first position wherein said knife blade is prevented from moving distally of said stapler, and a second position, said cartridge comprising:
   a cartridge body defining an elongated knife slot; and
   a rotatable member movable from a first position to a second position, wherein in said first position, said rotatable member engageable with said knife blade as said cartridge is positioned on the frame to move said knife blade from said first position to said second position thereof, said rotatable member being moved to said second position thereof by said knife blade as said knife blade is advanced distally of said cartridge through said knife slot, said rotating member including a resiliently flexible portion yieldably engageable with said cartridge body as said rotatable member is moved from said first position to said second position thereof, said flexible portion thereafter being engageable with said cartridge body to maintain said rotatable member in said second position thereof.

6. A staple cartridge in accordance with claim 5, wherein a first end portion of said rotatable member is pivotally mounted on said cartridge body, and said flexible portion of said rotatable member comprises a cantilevered arm at said first end portion.

7. A staple cartridge in accordance with claim 5, wherein said rotatable member comprises a cam projection engageable by said knife blade as said knife blade is advanced distally through said knife slot to facilitate movement of said rotatable member to said second position thereof.

8. A staple cartridge in accordance with claim 5, wherein said rotatable member comprises an integral, bifurcated pivot pin for pivotally mounting said rotatable member on said cartridge body.

* * * * *